United States Patent
Farthouat et al.

[11] 3,944,555
[45] Mar. 16, 1976

[54] N-(QUINOLYN)-ANTHRANILATES

[75] Inventors: Anne Farthouat, Romainville; Jean Meier, La Varenne Saint-Hilaire, both of France

[73] Assignee: Roussel Uclaf, Paris, France

[22] Filed: May 31, 1974

[21] Appl. No.: 474,885

[30] Foreign Application Priority Data
June 13, 1973  France .................. 73.21434

[52] U.S. Cl. ........ 260/287 AR; 260/286 R; 424/258
[51] Int. Cl.² ......................................... C07D 215/44
[58] Field of Search ................ 260/287 R, 287 AR

[56] References Cited
UNITED STATES PATENTS

| | | | |
|---|---|---|---|
| 2,940,974 | 6/1960 | Surrey .............................. | 260/286 R |
| 3,150,047 | 9/1964 | Allais et al. ..................... | 260/287 R |
| 3,174,972 | 3/1965 | Allais et al. ..................... | 260/287 R |

*Primary Examiner*—R. Gallagher
*Assistant Examiner*—David E. Wheeler
*Attorney, Agent, or Firm*—Hammond & Littell

[57] ABSTRACT

N-(7- or 8-substituted-quinolyl-4)-anthranilates of the formula

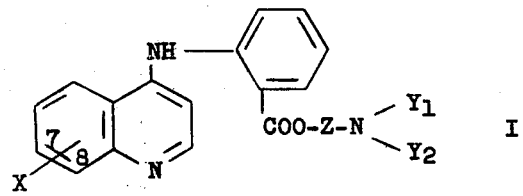

wherein X in the 7 or 8 position is trihalomethyl or trihalomethylthio, Z is $-(CH_2)_n-$ or $-(CH_2)_m-O-(CH_2)_p-$, $n$ is a whole number from 2 to 6, $m$ and $p$ are whole numbers from 2 to 3 and $Y_1$ and $Y_2$ are alkyl having 1 to 6 carbon atoms, as well as their non-toxic, pharmaceutically acceptable acid addition salts having analgesic and anti-inflammatory activity and their preparation.

7 Claims, No Drawings

N-(QUINOLYN)-ANTHRANILATES

OBJECTS OF THE INVENTION

It is an object of the invention to provide the novel anthranilates of the above formula I and their acid addition salts.

It is another object of the invention to provide a novel process for the preparation of the anthranilates of the above formula I.

It is a further object of the invention to provide novel analgesic and anti-inflammatory compositions.

It is an additional object of the invention to provide a novel method of treating pain and inflammation in warm-blooded animals.

These and other objects and advantages of the invention will become more apparent in the following description of the invention.

DESCRIPTION OF THE INVENTION

The novel compounds of the invention are selected from the group consisting of N-(7- and 8-substituted-quinolyl-4)-anthranilates of formula I:

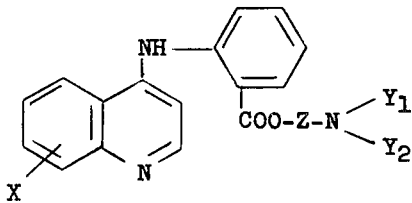

wherein X, in the 7 or 8 position, represents a trihalomethyl or trihalomethylthio group, Z represents the $-(CH_2)_n-$ group or the $-(CH_2)_m-O-(CH_2)_p-$ group, $n$ being a whole number between 2 and 6, $m$ and $p$ being whole numbers between 2 and 3, and $Y_1$ and $Y_2$ represent alkyl groups having 1 to 6 carbon atoms, as well as their non-toxic pharmaceutically acceptable acid addition salts.

In the formula I, the substituent X, which is preferably in the 8 position, particularly represents the trifluoromethyl or trifluoromethylthio group, most preferably the 8-trifluoromethyl; $n$ represents particularly the entire numbers 2, 3 or 4, preferably 2 or 3; and the substituents $Y_1$ and $Y_2$ preferably represent alkyl having from 1 to 4 carbon atoms, particularly methyl, ethyl, n-propyl, isopropyl, n-butyl or isobutyl.

More particularly the compounds of the invention are substituted anthranilates selected from the group consisting of N-(7- or 8-substituted-quinolyl-4)-anthranilates of the formula

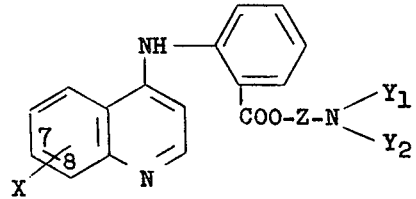

wherein X is a member in the 7 or 8 position selected from the group consisting of trihalomethyl and trihalomethylthio, Z is a member selected from the group consisting of $-(CH_2)_n-$, where $n$ is an integer from 2 to 6, and $-(CH_2)_m-O-(CH_2)_p-$, where $m$ and $p$ are each an integer from 2 to 3, and $Y_1$ and $Y_2$ are alkyl having from 1 to 6 carbon atoms, and their non-toxic, pharmaceutically acceptable acid addition salts.

Among the more interesting compounds of formula I as well as their acid addition salts are:

β-dimethylaminoethyl N-(8-trifluoromethyl-quinolyl-4)-anthranilate, and its dihydrochloride, γ-dimethylaminopropyl N-(8-trifluoromethyl-quinolyl-4-anthranilate, and its dihydrochloride, β-dibutylaminoethyl N-(8-trifluoromethyl-quinolyl-4)-anthranilate, and its dihydrochloride, β-(2'-diethylamino-ethoxy)-ethyl N-(8-trifluoromethyl-quinolyl-4)-anthranilate, and its dihydrochloride, as are described hereafter in Examples 1 to 8.

The novel compounds of formula I and their acid addition salts possess remarkable anti-inflammatory and analgesic activity. They are useful as therapeutics, for example, in the treatment of muscular, articular or nervous algias, of dental pains and of migraine headaches, as well as of inflammatory reactions, particularly of rheumatic disturbances, of lumbagos, of zonas, and also in the complementary treatment of infectious or febrile states. Thus the compounds of formula I, as well as their pharmaceutically acceptable acid addition salts, can be employed as medicaments.

Examples of suitable acids for the non-toxic pharmaceutically acceptable acid addition salts are mineral acids such as hydrochloric acid, hydrobromic acid, sulfuric acid, phosphoric acid, etc. and organic carboxylic acids such as acetic acid, benzoic acid, tartaric acid, citric acid, maleic acid, malonic acid, fumaric acid, etc., or organic sulfonic acids, such as methanesulfonic acid or p-toluenesulfonic acid, etc.

The anti-imflammatory and analgesic compositions of the invention are comprised of at least one compound of formula I or its non-toxic, pharmaceutically acceptable acid addition salt and a major amount of a pharmaceutical carrier. These pharmaceutical compositions may be administered parenterally, orally or rectally, or locally in a topical application on the skin or mucous membranes.

To this effect, the pharmaceutical compositions may be in the form of injectable solutions or suspensions, of tablets, of capsules, of gelules, of drinkable solutes or emulsions, of suppositories, of pomades, or of topical creams or powders. These pharmaceutical forms are prepared according to the usual methods.

The novel method of treating pain and inflammations in warm-blooded animals comprises administering to warm-blooded animals a safe and effective amount of at least one compound of formula I or its non-toxic, pharmaceutically acceptable acid addition salts. The said compounds may be administered orally, perlingually, transcutaneously, rectally or topically on skin or mucous membranes. The usual useful daily dose is 0.9 to 5 mg/kg depending upon the method of administration. The total daily dose in the adult, for example, can be varied between 100 and 500 mg of active principle, when administered orally.

The compounds of formula I can be prepared according to the usual processes for the preparation of esters. In particular, the compounds of formula I are prepared by a process which is characterized in that a functional derivative of an acid of the formula II:

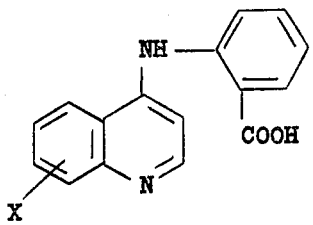

wherein X has the above-assigned values, and particularly a lower alkyl ester, acid chloride, acid anhydride or mixed anhydride, is reacted with an alcohol of the formula III:

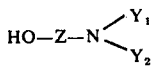

wherein Z, $Y_1$ and $Y_2$ have the above-assigned values. The acid addition salts of the compounds of formula I are prepared according to the usual methods.

The starting compounds of formulas II and III are either described in the literature, or accessible by means of general methods described in the literature. Compounds of formula II can be prepared by the processes described in Belgian Patent 710,321, or French Patent 1,369,967 or copending commonly assigned U.S. Patent application Ser. No. 830,148, filed June 3, 1969.

In the following examples there are described several preferred embodiments to illustrate the invention. However, it should be understood that the invention is not intended to be limited to the specific embodiments.

EXAMPLE 1

β-dimethylaminoethyl
N-(8-trifluoro-methyl-quinolyl-4)-anthranilate 50 cc of anhydrous dimethylaminoethanol, 150 mg of an oil suspension containing 50% of sodium hydride and 10 gm of methyl N-(8-trifluoromethyl-quinolyl-4)-anthranilate were mixed together. The mixture was heated for four hours at 90° to 95°C under a slightly reduced pressure, then cooled to room temperature. 50 cc of methylene chloride, 100 cc of water and 5 cc of a saturated aqueous solution of ammonium chloride were added thereto. The organic phase was separated, washed with water, and evaporated to dryness. The residue was dissolved in 150 cc of isopropyl ether, treated with activated carbon black, filtered and the isopropyl ether was concentrated.

6.3 gm of β-dimethylaminoethyl N-(8-trifluoromethyl-quinolyl-4)-anthranilate was obtained, crystallized in the form of prisms melting at 86°C.

In other productions, the product crystallized in the form of needles melting at 96°C.

These two crystalline forms act identically in thin layer chromatography and infrared spectrometry.

EXAMPLE 2

β-dimethylaminoethyl
N-(8-trifluoromethyl-quinolyl-4)-anthranilate
dihydrochloride The dihydrochloride is obtained by the addition of a methanolic solution of hydrochloric acid to a methanolic solution of the product obtained in the preceding example. By the addition of isopropyl ether, the dihydrochloride precipitated. It had a melting point of 195°C.

EXAMPLE 3

γ-dimethylaminopropyl
N-(8-trifluoromethyl-quinolyl-4)-anthranilate 50 cc of anhydrous γ-dimethylaminopropanol, 150 mg of an oil suspension containing 50% of sodium hydride and 10 gm of methyl N-(8-trifluoromethyl-quinolyl-4)-anthranilate were mixed. This mixture was heated for four hours to 90° to 95°C under reduced pressure (8 to 9 cm of Hg). The reaction mixture was then allowed to stand overnight. Then 90 cc of water were added and the reaction mixture was cooled to 0°C. for twenty minutes. The precipitate formed was separated, redissolved in isopropyl ether, treated with activated carbon and recrystallized. γ-dimethylaminopropyl N-(8-trifluoromethyl-quinolyl-4)-anthranilate was obtained, having a melting point of 120°C.

EXAMPLE 4

γ-dimethylaminopropyl
N-(8-trifluoromethyl-quinolyl-4)-anthranilate
dihydrochloride The dihydrochloride was obtained by the addition of a methanolic solution of hydrochloric acid to a suspension in methanol of the product obtained in the preceding example. On addition of isopropyl ether, the dihydrochloride precipitated. It had a melting point of 186°C.

EXAMPLE 5

β-dibutylaminoethyl
N-(8-trifluoromethyl-quinolyl-4)-anthranilate

By the action of thionyl chloride on N-(8-trifluoromethyl-quinolyl-4)-anthranilic acid, the corresponding acid chloride was prepared. Five times the theoretical amount of β-dibutylaminoethanol was added to this acid chloride while agitating at room temperature until complete dissolution.

The reaction mixture was added to water, agitated and then extracted with ether. The ethereal extract was washed, dried and evaporated to dryness under reduced pressure. By chromatography through silica gel with elution by the mixture ether-petroleum ether (b.p. 64° to 75°C)-triethylamine (5:5:0.5) and collecting the Rf:0.35 fractions, β-dibutylaminoethyl N-(8-trifluoromethyl-quinolyl-4)-anthranilate was obtained in the form of a crystallized product having a melting point below 50°C.

EXAMPLE 6

β-dibutylaminoethyl
N-(8-trifluoromethyl-quinolyl-4)-anthranilate
dihydrochloride The dihydrochloride was obtained by the addition of a methanolic solution of hydrochloric acid to a methanolic solution of the product obtained in the preceding example. By the addition of isopropyl ether, the dihydrochloride precipitated. It had a melting point of 185°C.

EXAMPLE 7

β-(2'-diethylaminoethoxy)-ethyl N-(8-trifluoromethyl-quinolyl-4)-anthranilate 64 cc of β-(2-diethylaminoethoxy)-ethanol were heated to 50°C and 300 mg of an oily suspension containing 50% sodium hydride and 20 gm of methyl N-(8-trifluoromethyl-quinolyl-4)-anthranilate were added thereto. The mixture was heated to 85°C under a reduced pressure of 50 mm of mercury for four hours. The reaction mixture was then cooled to 20°C and poured into 350 cc of water. The precipitate formed was separated.

On recrystallization from isopropyl ether, β-(2'-diethylaminoethoxy)-ethyl N-(8-trifluoromethyl-quinolyl-4)-anthranilate was obtained, melting at 72°C.

EXAMPLE 8

β-(2'-diethylaminoethoxy)-ethyl N-(8-trifluoromethyl-quinolyl-4)-anthranilate dihydrochloride The dihydrochloride is obtained by the addition of a methanolic solution of gaseous hydrogen chloride to a methanolic solution of the product obtained in the preceding example. By the addition of isopropyl ether, the dihydrochloride precipitated. It had a melting point of about 140°C.

EXAMPLE 9

Preparation of Tablets

Tablets were prepared corresponding to the following formula:

| | |
|---|---|
| Compound of Example 1 | 50 mg |
| Excipient sufficient for 1 tablet containing | 350 mg |

The excipient consisted of starch, lactose, talc and magnesium stearate.

Any of the compounds of the other examples or those included in the generic formula I can be substituted in the above formula with the same results.

PHARMACOLOGICAL DATA

1. Anti-Inflammatory Effect: Naphthoylheparamine Test

The principle of the test employed is that described by Jequier et al, Arch. Int. Pharmacodyn., 152, p. 15 (1954).

This consists in administering 1 mg of naphthoylheparamine in one single injection to the hind paws of rats weighing about 150 gm. This provokes the formation of an inflammatory edema. The products being studied were administered orally in an aqueous suspension one hour before the irritant injection.

The volume of the paw is measured immediately before and two hours after the irritant injection. The increase of the volume of the paw represents a measure of the degree of inflammation. Next, the $DA_{40}$, that is the dose which diminishes the degree of inflammation by 40% with reference to the controls, is determined.

2. Analgesic Effect: Acetic Acid Test

The test employed was based on the fact noted by Koster et al. (Fed. Proc. 1959, 18, 412) according to which the intraperitoneal injection of acetic acid provoked repeated characteristic movements of stretching and twisting which persisted in mice for more than six hours. Analgesics prevent or suppress this syndrome which is an exterior manifestation of a diffuse abdominal pain.

A solution of 6 parts per thousand of acetic acid in water containing 10% of arabic gum was employed and the dose provoking the syndrome in mice under these conditions was 0.01 cc/gm, being 60 mg/kg of acetic acid.

The analgesics were administered orally to groups of five mice, which had not been fed for 24 hours, a half hour before the intraperitoneal injection of the acetic acid. The stretchings were observed, noted and counted for each mouse, during a period of observation of fifteen minutes immediately after the injection of acetic acid.

The results are expressed on the basis of the $DA_{50}$, that is, the dose which permits obtaining a 50% diminution of the number of stretchings with reference to the control animals.

The results of the two tests are given in the Table.

TABLE

| Compound of Example | Anti-Inflammatory Effect $DA_{40}$ mg/kg | Analgesic Effect $DA_{50}$ mg/kg |
|---|---|---|
| 1 | 8 | 7 |
| 2 | 7 | 8 |
| 4 | 20 | 20 |
| 6 | 11 | 8 |
| 8 | 3 | 8 |

The preceding specific embodiments are illustrative of the practice of the invention. It is to be understood, however, that other expedients known to those skilled in the art or disclosed herein may be employed without departing from the spirit of the invention or the scope of the appended claims.

We claim:

1. Substituted anthranilates selected from the group consisting of N-(7- or 8-substituted-quinolyl-4)-anthranilates of the formula

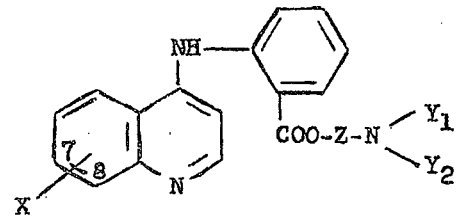

wherein X is trifluoromethyl in the 7 or 8 position, Z is a member selected from the group consisting of $-(CH_2)_n-$, where $n$ is an integer from 2 to 6, and $-(CH_2)_m-O-(CH_2)_p-$, where $m$ and $p$ are each an integer from 2 to 3, and $Y_1$ and $Y_2$ are alkyl having from 1 to 6 carbon atoms, and their non-toxic, pharmaceutically acceptable acid addition salts.

2. The substituted anthranilates of claim 1 wherein $Y_1$ and $Y_2$ are alkyl having from 1 to 4 carbon atoms.

3. The substituted anthrianilates of claim 2 wherein X is 8-trifluoromethyl and $n$ is an integer from 2 to 4.

4. Substituted anthranilates of claim 3 selected from the group consisting of β-dimethylaminoethyl N-(8-trifluoromethyl-quinolyl-4)-anthranilate and its dihydrochloride.

5. Substituted anthranilates of claim 3 selected from the group consisting of γ-dimethylaminopropyl N-(8-trifluoromethyl-quinolyl-4)-anthranilate and its dihydrochloride.

6. Substituted anthranilates of claim 3 selected from the group consisting of β-dibutylaminoethyl N-(8-trifluoromethyl-quinolyl-4)-anthranilates and its dihydrochloride.

7. Substituted anthranilates of claim 2 selected from the group consisting of β-(2'-diethylamino-ethoxy)ethyl N-(8-trifluoromethyl-quinolyl-4)-anthranilate and its dihydrochloride.

* * * * *